United States Patent [19]

Okey

[11] 4,159,243

[45] Jun. 26, 1979

[54] PROCESS AND SYSTEM FOR CONTROLLING AN ORBITAL SYSTEM

[75] Inventor: Robert W. Okey, Covina, Calif.

[73] Assignee: Envirotech Corporation, Menlo Park, Calif.

[21] Appl. No.: 823,068

[22] Filed: Aug. 9, 1977

[51] Int. Cl.² .............................................. C02C 1/06
[52] U.S. Cl. ....................................... 210/14; 210/16; 210/199; 210/96.1; 210/DIG. 28
[58] Field of Search .................... 210/DIG. 28, 8, 14, 210/15, 16, 96 R, 199, 194, 195 R

[56] References Cited

U.S. PATENT DOCUMENTS

| 3,426,899 | 2/1969 | Smith | 210/96 R |
|---|---|---|---|
| 3,557,954 | 1/1971 | Welch | 210/96 R |
| 3,900,394 | 8/1975 | Rongved | 210/DIG. 28 |
| 3,964,998 | 6/1976 | Barnard | 210/DIG. 28 |
| 3,977,965 | 8/1976 | Tholander et al. | 210/DIG. 28 |

OTHER PUBLICATIONS

Van Der Geest; A. T. et al., "Nitrification and Denitrification in Carrousel Systems", presented at W.P.C.F. annual meeting, 1975.

Primary Examiner—Benoit Castel
Attorney, Agent, or Firm—Hal J. Bohner; Robert E. Krebs

[57] ABSTRACT

The present process and system provides a means for controlling denitrification in an orbital system. The process includes measuring the dissolved oxygen concentration at two or more points in the sewage in the orbital system and controlling the rate of aeration of the sewage according to the dissolved oxygen concentration.

3 Claims, 8 Drawing Figures

PROCESS AND SYSTEM FOR CONTROLLING AN ORBITAL SYSTEM

BACKGROUND OF THE INVENTION

1. Field of the Invention

This invention relates to a method and a system for removing impurities from sewage.

2. State of the Art

Sewage often contains a number of impurities which include materials such as sugars and other carbohydrates, and proteins and other forms of nitrogen. Many of these impurities are decomposed by micro-organisms, and oxygen in the sewage is used by the microorganisms to accomplish the decomposition. Therefore, the impurities are generally called oxygen-demanding, and they are said to produce a biochemical or nitrogenous oxygen demand, depending upon their chemical composition.

Ammonia and many chemicals containing organic nitrogen are decomposed and oxidized according to the process of nitrification to produce compounds containing nitrates. Often, it is desirable to remove the nitrates from the sewage, and this is accomplished according to the process of denitrification.

A conventional sewage treatment system, called an orbital system, is taught in U.S. Pat. No. 3,510,110. Another orbital system is taught in a paper entitled, "Nitrification and Denitrification in Carrousel Systems," by Anton T. van der Geest and William C. Witvoet, presented at the annual meeting of the Water Pollution Control Federation in 1975. The orbital system taught in the paper by van der Geest and Witvoet operates to accomplish nitrification and denitrification and includes a control system to control the extent to which nitrification and dentrification take place. However, the control system is unable to operate effectively if the characteristics of the sewage fluctuate substantially.

OBJECTS OF THE INVENTION

An object of the present invention is to provide a process and a system to control the operation of an orbital sewage treatment system, the control process and system being capable of effective operation over a wide range of sewage characteristics.

BRIEF DESCRIPTION OF THE DRAWINGS

Further objects of the present invention may be readily determined by reference to the following description and appended drawings, which are offered by way of example only and not in limitation of the invention, the scope of which is defined by the appended claims and equivalents to the structure, materials and acts set forth hereinafter. In the drawings:

DETAILED DESCRIPTION OF THE PREFERRED EMBODIMENT

Figure 1:
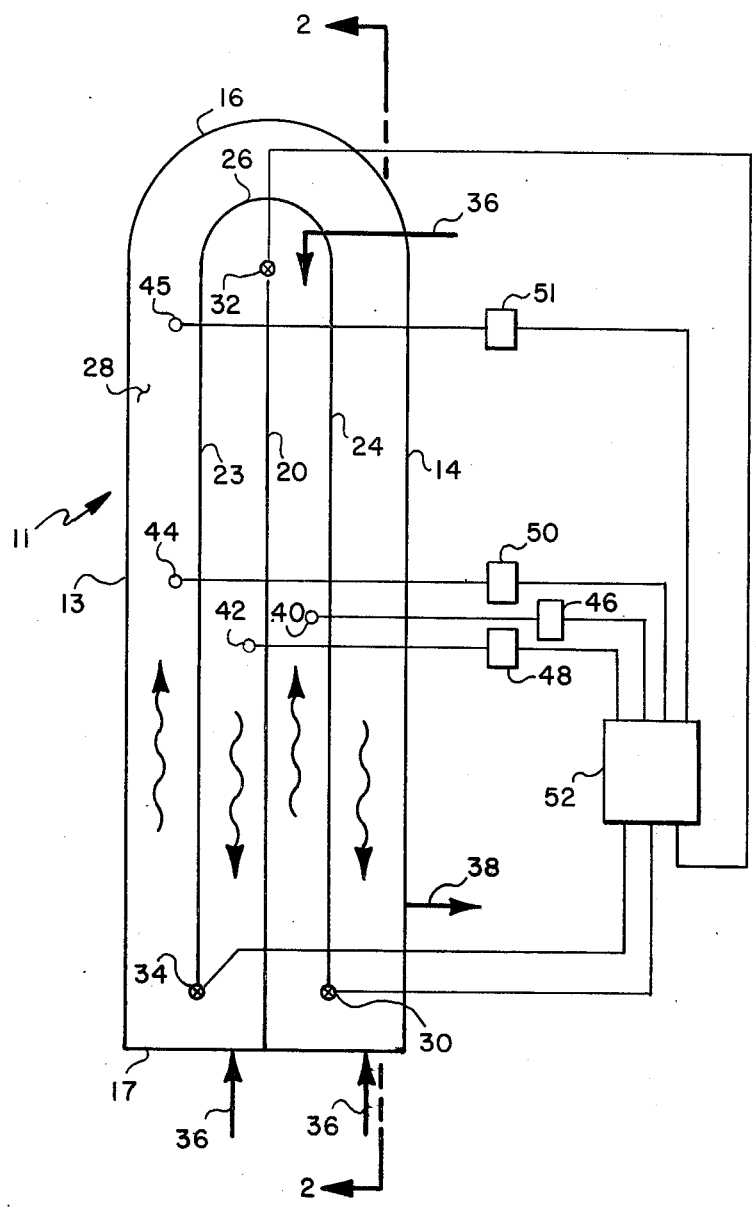
FIG. 1 is a plan view of the preferred embodiment of the present invention.
Figure 2:
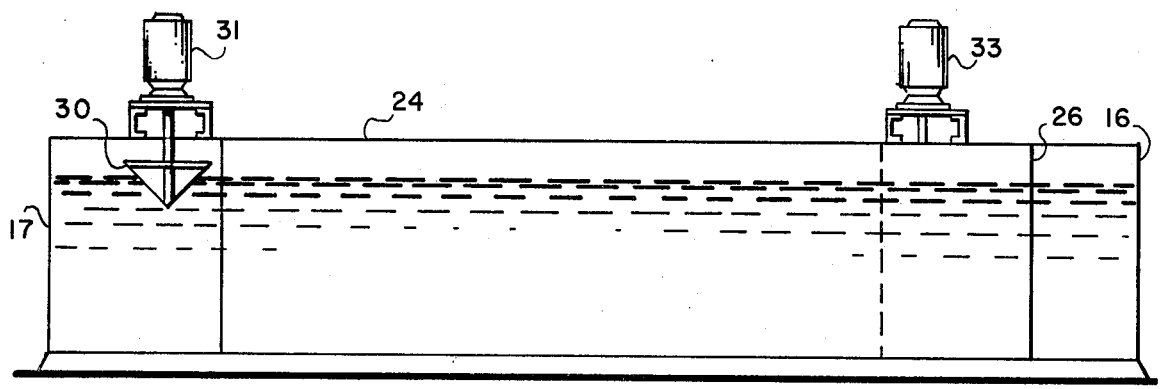
FIG. 2 is a sectional view of the apparatus shown in FIG. 1 and taken along line 2—2.

The orbital sewage treatment system shown in FIGS. 1 and 2 includes an elongated liquid-holding tank 11 having a bottom, upstanding sidewalls 13 and 14, and opposed endwalls 16 and 17. An upstanding partition wall 20 is fixedly mounted medially in the tank to extend lengthwise thereof with one end spaced apart from endwall 16 and the other end connected to endwall 17. The partition wall 20 thus divides the tank 11 into two straight sections which are in fluid flow communication at the end of the tank near endwall 16.

An upstanding partition wall 23 is mounted in the tank and spaced apart from endwalls 16 and 17 to form two channels between partition wall 20 and sidewall 13. An upstanding partition wall 24 is mounted in the tank and spaced apart from the endwalls 16 and 17 to form two channels between partition wall 20 and sidewall 14. A curved endwall 26 is mounted in the tank near endwall 16 and is connected to the ends of the partition walls 23 and 24. The partition walls and end walls form a circuitous, endless channel 28 which has four straight legs. Other orbital configurations than that disclosed may be employed, for example, those shown in the above-identified paper by van der Geest and Witvoet.

Mounted within the tank between the ends of partition walls 23 and 24 and endwall 17 are means for agitating the sewage to mix air with it and to impell the sewage to flow through the channel 28 as indicated by the arrows. The illustrated aerating and impelling means are conventional surface-type aerators 30 and 34 which are driven to rotate by drive units 31 and 35 mounted above the tank. The drive units 31 and 35 are controllable to drive the aerators at one of a plurality of speeds, say three speeds, or infinitely variable speeds, depending upon the application of control signals discussed hereinafter. A third aerator 32 is mounted within the tank between the end of partition wall 20 and curved endwall 26; the third aerator is driven by a controllable, multi-speed drive unit 33.

Three influent conduits 36 are connected to the tank to introduce sewage at one or more locations near each of the aerators 30, 32 and 34. An effluent conduit 38 is connected to the tank 11 through sidewall 14 to remove sewage from the tank.

Dissolved oxygen probes 40, 42 and 44 are disposed in the channel 28, respectively, between partition walls 24 and 20, between partition walls 20 and 23, and between partition wall 23 and sidewall 13. Dissolved oxygen probe 45 is disposed in the channel 28 between partition wall 23 and sidewall 13 nearer the endwall 16 than dissolved oxygen probe 44. The dissolved oxygen probes 40, 42, 44 and 45 are conventional and transmit electrical signals proportional to the concentration of oxygen dissolved in the liquid in which they are immersed. These probes are manufactured, for example, by Beckman Instruments, Inc. The electrical signals from the dissolved oxygen probes are transmitted, respectively, to amplifiers 46, 48, 50 and 51 which, in turn, transmit the amplified electrical signals to controller 52. The controller 52, which for example, can include a programmable mini-computer, receives the signals from the amplifiers 46, 48, 50 and 51 and transmits electrical signals to the drive units 31, 33 and 35 to control the speed at which the aerators are driven.

Figure 3:
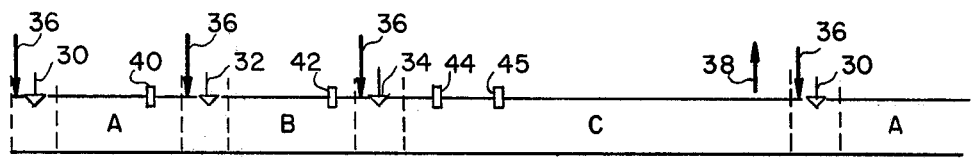
FIG. 3 is a diagram corresponding to a linear projection of the length of the channel of the apparatus shown in FIG. 1.

The operation of the present invention will be described with reference to FIG. 3 which is a diagram corresponding to a linear projection of the channel 28. For simplicity the length of channel 28 has been shortened from that shown in FIG. 1. Generally, sewage is introduced into the channel 28 through the three influent conduits 36; however, sewage can be introduced through any one or more of the influent conduits. The aerators 30, 32 and 34 rotate to cause the sewage to flow in the direction indicated by the arrow. Part of the treated, denitrified sewage in the channel is removed via line 38 and transferred to further treatment such as a clarifier, and thence to a receiving water. The remainder of the sewage, which normally would be a major portion, continues to flow along the channel and returns to aerator 30. The part of the channel downstream of aerator 30 is designated herein as zone "A". Downstream of zone "A" and aerator 32 and upstream of aerator 34 is designated zone "B", and downstream of zone "B" and upstream of aerator 30 is designated zone "C" wherein effluent conduit 38 is located.

Figure 4:
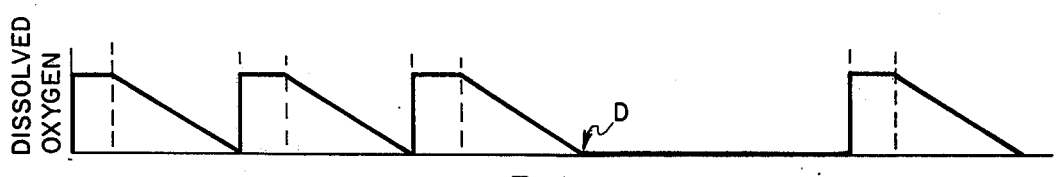
FIGS. 4 through 8 are graphs corresponding to FIG. 3, showing dissolved oxygen concentration in the sewage versus distance along the channel.
Figure 5:
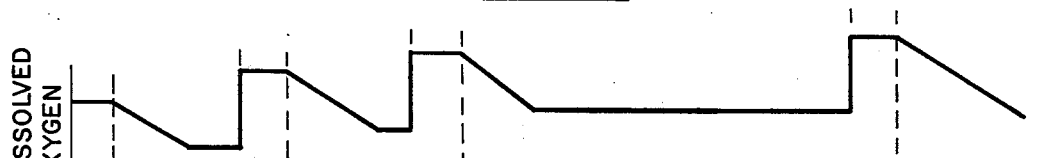

Beginning at aerator 30, for the purpose of the following illustration, the stream of sewage flowing through the channel 28 is aerated by aerator 30 so that oxygen is dissolved. Micro-organisms in the sewage decompose oxygen-demanding impurities and consume dissolved oxygen, and therefore, the concentration of dissolved oxygen decreases as the sewage travels downstream through zone "A", as shown in FIG. 4. When the sewage flows beneath aerator 32 additional air is mixed with the sewage, and therefore, the concentration of dissolved oxygen increases. Likewise, the dissolved oxygen decreases as the sewage flows through zone "B" and, after the action of aerator 34, again decreases in zone "C", as shown in FIG. 4.

According to FIG. 4, throughout most of zones "A" and "B" the sewage contains a substantial concentration of dissolved oxygen up to the location of the most downstream aerator and is therefore termed aerobic. Zone "C" is longer than zone "A" or "B", and therefore, the dissolved oxygen is substantially depleted in the upstream, aerobic part of the zone. In the part of zone "C" downstream of point "D" the sewage is substantially devoid of dissolved oxygen and is therefore termed anoxic. This is the denitrification part of zone "C".

During the time the sewage is aerobic, the dissolved oxygen is utilized by micro-organisms to decompose oxygen-demanding impurities which do not contain nitrogen. The dissolved oxygen is also utilized by nitrifying micro-organisms, to convert ammonia and other nitrogen-containing compounds to nitrates, say by the following reaction:

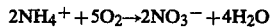
$$2NH_4^+ + 5O_2 \rightarrow 2NO_3^- + 4H_2O$$

This reaction is generally known as nitrification, wherein $NH_4^+$ denotes ammonium ions; $O_2$ denotes oxygen; $NO_3^-$ denotes nitrate ions; and $H_2O$ denotes water.

Under anoxic conditions, micro-organisms act upon nitrate ions in the sewage and facilitate the following reaction:

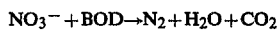
$$NO_3^- + BOD \rightarrow N_2 + H_2O + CO_2$$

This reaction, wherein $N_2$ denotes nitrogen gas and $CO_2$ denotes carbon dioxide gas, and BOD denotes oxygen-demanding impurities which do not contain nitrogen, is generally termed denitrification.

The time during which the sewage is anoxic determines the extent to which denitrification takes place. Therefore, if the concentration of nitrate in the effluent discharged through effluent conduit 38 must be maintained below a predetermined maximum, anoxic conditions must exist in a predetermined minimum part of zone "C". Similarly, the time during which the sewage is aerobic determines the extent to which decomposition of oxygen-demanding materials and nitrification takes place. The present orbital system is designed to operate substantially in accordance with the graph of FIG. 4 so that the distance downstream from point "D", where the sewage becomes anoxic, to the beginning of zone "A", is sufficient to insure that denitrification has taken place to reduce the nitrate concentration below the required maximum. The present orbital system is also designed so that adequate decomposition of oxygen-demanding impurities and nitrification also is insured.

The sewage introduced through influent conduits 36 is variable in its strength and its rate of flow, and these two parameters affect the strength of the sewage in the channel 28. The strength of sewage in the channel 28 is directly related to the amount of oxygen consumed by the micro-organisms in decomposing the oxygen-demanding impurities. When the sewage is weak, the amount of oxygen consumed by the micro-organisms per unit of length along the channel is low, and therefore, the slope of the dissolved oxygen profile is small. On the other hand, when the sewage is strong the slope of the dissolved oxygen profile is large. The rate of introduction of the sewage determines the quantity of oxygen-demanding impurities introduced into the channel 28; and, consequently, the strength of the sewage in the channel 28. When sewage is introduced at a high rate, a large quantity of oxygen-demanding impurities is introduced into the channel 28, and the sewage in the channel is strong. Therefore, when the quantity of oxygen-demanding impurities introduced into the channel is high, the slope of the dissolved oxygen profile is large, and vice versa.

Figure 6:
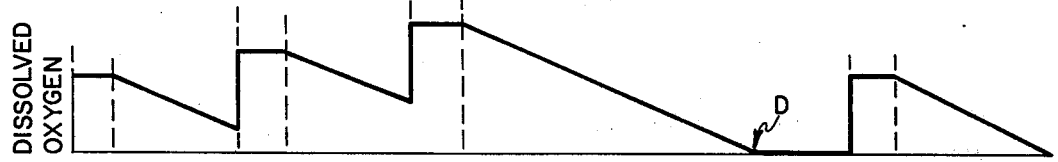

FIG. 6 shows the profile of dissolved oxygen when the sewage in the channel 28 is weaker than the sewage as illustrated in FIG. 4. According to FIG. 6, it can be seen that if weak sewage is present in the channel, point "D" would move downstream, if the aerators 30, 32 and 34 were operated at their highest speeds. However, the controller operates to insure that point "D" does not move downstream to reduce the zone of denitrification below an acceptable level.

The controller 52 utilizes the dissolved oxygen concentrations measured by probes 40 and 42 and controls the speed of aerators 30 and 32 to insure that zones "A" and "B" are aerobic throughout and that the aerators are not operated at a higher speed than necessary to maintain the zones aerobic. For example, if the sewage becomes weak, the dissolved oxygen concentration tends to increase, and consequently the controller 52 reduces the speed of aerators 30 and 32 as necessary to maintain zones "A" and "B" aerobic throughout.

Figure 8:
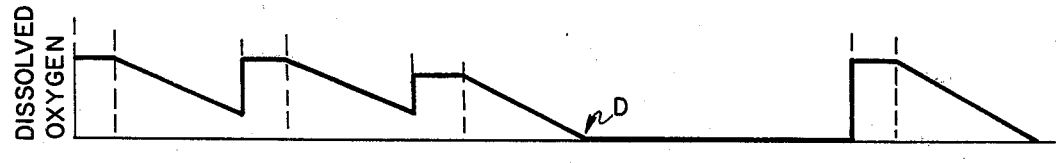

The controller 52 also compares the dissolved oxygen concentrations measured by probes 44 and 45 and continuously determines the slope of the dissolved oxygen profile in the aerobic part zone "C". The controller 52 also utilizes the dissolved oxygen concentration measured by probe 44. If the slope of the dissolved oxygen profile and the dissolved oxygen concentration at probe 44 are such that point "D" is too far downstream, the controller reduces the speed of one or more drive units according to a predetermined control sequence. For example, according to one control sequence the controller 52 causes the drive unit 35 to operate at the first speed slower than its highest speed. Consequently, the amount of oxygen dissolved in the sewage by aerator 34 is less than if the aerator were at its highest speed, and point "D" is moved upstream. If reduction of the drive unit 35 to the first slower speed does not reduce the dissolved oxygen concentration enough to result in a sufficient zone of denitrification, the controller 52 takes the next step in the control sequence and causes the aerator 32 to operate one speed below its highest speed thus causing point "D" to move further upstream. After these two steps of the control sequence, the dissolved oxygen profile is as shown in FIG. 8. If point "D" is not sufficiently far upstream, the controller reduces the speed of aerator 30 and thereafter reduces the speed of aerators 32 and 34 step-by-step until point "D" has been moved to the desired location. As heretofore stated, the speed control may be continuously variable rather than variable in steps.

When the drive units are operating below their highest speed, and the dissolved oxygen concentration measured by probes 44 and 45 decreases below the concentration necessary to maintain point "D" in the proper location, the controller operates according to a predetermined control sequence. For example, according to one control sequence, if the system is in the FIG. 8 condition and the rate of flow of the sewage increases so that point "D" begins to move too far upstream, the controller increases the speed of aerator 34 step-by-step to cause point "D" to move downstream. If this control of aerator 34 does not move point "D" sufficiently far downstream, the controller increases the speed of aerators 32 and 30 step-by-step.

Figure 7:
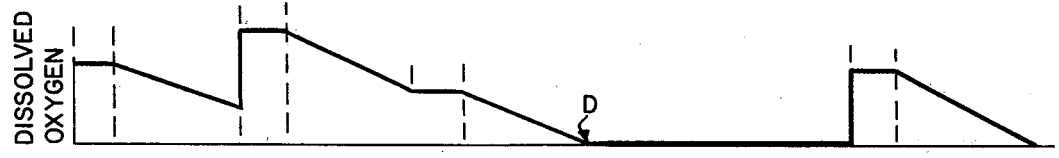

According to another predetermined control sequence, the controller 52 reduces the speed of aerator 34 step-by-step until it is completely shut off. As a result of this control sequence, the dissolved oxygen profile can be as shown in FIG. 7. However, if the application of this control sequence does not cause point "D" to move sufficiently far upstream, the controller 52 takes further steps reducing the speed of the aerators 32 and 30, step-by-step.

Thus, it can be understood that the controller 52 controls the operation of the aerators 30, 32 and 34 to insure that sufficient denitrification occurs regardless of the strength of the sewage or the rate of introduction into the channel. The controller also insures that the aerators introduce sufficient oxygen into the sewage so that adequate aerobic decomposition of the oxygen-demanding impurities and nitrification takes place. Also, the controller 52 insures that the aerators do not operate at a speed higher than necessary to maintain adequate aerobic decomposition and nitrification, and thus operating costs are minimized. It can also be understood that the control system described above permits the orbital system to be designed and built with a minimum length thus resulting in minimization of capital cost.

It is understood that only two control sequences have been described and that the control system can be set to perform other control sequences. It should also be understood that in the discussion above, the rate of oxygenation of the sewage is controlled by controlling the speed of the aerators and that other conventional means of varying the rate of oxygenation of the sewage can be utilized. For example, the aerators can be controllably raised or lowered to various depths in the sewage. It should further be understood that within the anoxic zones discussed above, anaerobic decomposition, as well as denitrification, often occurs.

I claim:

1. A process for treating sewage in the channel of an orbital system comprising:
   a. introducing a stream of sewage into the channel with the strength of the introduced sewage and the rate of introduction being variable;
   b. impelling the sewage to flow through the channel;
   c. aerating the sewage by a controllable aerator to introduce oxygen into the sewage to promote decomposition of oxygen-demanding impurities and to form a zone of nitrification and a zone of denitrification downstream from the zone of nitrification wherein the concentration of dissolved oxygen in the zone of nitrification decreases in the direction of flow thereby forming a dissolved oxygen profile, and the slope of the dissolved oxygen profile varies with varying strength of the introduced sewage, and the location of the zone of denitrification varies with the rate of flow of sewage through the channel and the slope of the dissolved oxygen profile;
   d. removing a partial stream of sewage from the sewage at a point within the zone of denitrification;
   e. measuring the dissolved oxygen profile with two probes, the first probe located in the zone of nitrification and the second probe located in the zone of nitrification and downstream of the first probe;
   f. transmitting signals from said two probes to a controller which utilizes the signals to:
      i. determine the slope of the dissolved oxygen profile between said first and said second probes;
      ii. determine, based on the slope of the dissolved oxygen profile and the signal from the first probe, the location of a point upstream of which the sewage is aerobic and downstream of which the sewage is anoxic;
      iii. determine the distance between the point and said controllable aerator;
      iv. compare the distance between the point and said controllable aerator with a predetermined maximum distance and generate a signal according to the compared distances; and
   g. transmitting the signal generated by said controller to said controllable aerator to control the aerator to aerate the sewage so that the distance between the point and the aerator is not greater than the predetermined maximum distance.

2. The process of claim 1 wherein said controllable aerator is controlled to aerate the sewage so that the distance between the point and the aerator is approximately equal to the predetermined minimum distance.

3. In a system for treating sewage in the channel of an orbital system the improvement comprising:
   a. controllable aeration means disposed in the channel for aerating the sewage to introduce oxygen into the sewage to promote decomposition of oxygen-demanding impurities and to form a zone of nitrification and a zone of denitrification downstream from the zone of nitrification wherein the concentration of dissolved oxygen in the zone of nitrification decreases in the direction of flow thereby forming a dissolved oxygen profile, and the slope of the dissolved oxygen profile varies with varying strength of the introduced sewage, and the location of the zone of denitrification varies with the rate of flow of sewage through the channel and the slope of the dissolved oxygen profile;

b. two probes for measuring the dissolved oxygen profile, the first probe disposed in the zone of nitrification and the second probe disposed in the zone of nitrification and downstream of the first probe;

c. control means coupled to receive signals from the two probes to:
 i. determine the slope of the dissolved oxygen profile between said first and said second probes;
 ii. determine, based on the slope of the dissolved oxygen profile and the signal from the first probe, the location of a point upstream of which the sewage is aerobic and downstream of which the sewage is anoxic;
 iii. determine the distance between the point and said controllable aerator;
 iv. compare the distance between the point and said controllable aerator with a predetermined maximum distance and generate a signal according to the compared distances; and d. means for transmitting the signal generated by said controller to said controllable aerator to control the aerator to aerate the sewage so that the distance between the point and the aerator is not greater than the predetermined maximum distance.

* * * * *